(12) United States Patent
Visel et al.

(10) Patent No.: US 7,597,788 B2
(45) Date of Patent: Oct. 6, 2009

(54) OXYGEN-CHEMICAL AGENT SENSOR

(75) Inventors: Thomas Visel, Austin, TX (US); Prabhu Soundarrajan, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 792 days.

(21) Appl. No.: 11/185,475

(22) Filed: Jul. 20, 2005

(65) Prior Publication Data

US 2007/0086921 A1 Apr. 19, 2007

Related U.S. Application Data

(60) Provisional application No. 60/589,408, filed on Jul. 20, 2004.

(51) Int. Cl.
*G01N 27/403* (2006.01)
(52) U.S. Cl. .................. 204/400; 204/431; 205/775; 977/957; 422/82.01
(58) Field of Classification Search .................. 204/400, 204/403.01, 412, 426, 431; 205/775, 786.5, 205/780, 792; 977/957; 422/82.01–82.04
See application file for complete search history.

(56) References Cited

U.S. PATENT DOCUMENTS

| | | | |
|---|---|---|---|
| 5,572,031 A | 11/1996 | Cooper et al. | 250/343 |
| 6,528,020 B1 * | 3/2003 | Dai et al. | 422/98 |
| 6,946,693 B1 * | 9/2005 | Scheible et al. | 257/213 |
| 7,052,588 B2 * | 5/2006 | Gu et al. | 204/403.01 |
| 2003/0089899 A1 * | 5/2003 | Lieber et al. | 257/9 |

OTHER PUBLICATIONS

Sotiris Sotiropoulos et al., "Solid-state microelectrode oxygen sensors," *Analytica Chimica Acta*, 388, 1999, pp. 51-62.
"Appendix B About Hydrocarbons," *Aviation Fuels Technical Review*, 2000, pp. 82-85.
Philip G. Collins et al., "Extreme Oxygen Sensitivity of Electronic Properties of Carbon Nanotubes," *Science*, Mar. 10, 2000, vol. 287, pp. 1801-1804.
George E. Froudakis et al., "Pathways for oxygen adsorption on single-wall carbon nanotubes," *Physical Review*, B 68, 2003, pp. 1-5.
Andrea Goldoni et al., "Single-Wall Carbon Nanotube Interaction with Gases: Sample Contaminants and Environmental Monitoring," *JACS Articles*, 2003, 125, pp. 11329-11333.

(Continued)

*Primary Examiner*—Kaj K Olsen
*Assistant Examiner*—Bach T Dinh
(74) *Attorney, Agent, or Firm*—Fish & Richardson P.C.; Kelly Kordzik (57) ABSTRACT

A gas sensing mechanism and a gas sensor based on a semiconducting carbon nanotube diode structure are disclosed. The gas sensor operates by detecting the change in conductivity characteristic of the current vs. voltage behavior of an I—N, or I—P junction, in the carbon nanotube. In the presence of electrophilic gas species at the I—N junction, or nucleophilic gas species at the I—P junction, a P—N, or N—P, junction is created by doping of the carbon nanotube by the respective gas species. The resulting change from the undoped, instrinsic i-type to p-type, or n-type, creates a diode structure whose conductivity characteristics can be measured with high accuracy and selectivity.

16 Claims, 7 Drawing Sheets

OTHER PUBLICATIONS

M. Grujicic et al., "The effect of topological defects and oxygen adsorption on the electronic transport properties of single-walled carbon-nanotubes," *Applied Surface Science*, 211 2003, pp. 166-183.

Jing Kong et al., "Chemical profiling of single nanotubes: Intramolecular p-n-p junctions and on tube single-electron transistors," *Applied Physics Letters*, vol. 80, No. 1, Jan. 7, 2002, pp. 73-75.

Kwanyong Seo et al., "Tuning Chirality of Single-Wall Carbon Nanotubes by Selective Etching with Carbon Dioxide," *JACS Communications*, 2003, 125, 13946-13947.

J.P. Novak, et al., "Nerve agent detection using networks of single-walled carbon nanotubes," *Applied Physics Letters*, vol. 83, No. 19, Nov. 10, 2003, pp. 4026-4028.

De Castro et al., "Reliable, maintenance-free oxygen sensor for aircraft using an oxygen-sensitive coating on potentiometric electrodes,". Abstract, p. 1, 1990, available via the Internet at http://www.stormingmedia.us/69/6962/A696222.html.

Hendrik Ulbricht et al., "Interaction of molecular oxygen with single-wall carbon nanotube bundles and graphite," *Surface Science*, 532-535, 2003, pp. 852-856.

Stephen P. Walch, "On the reaction of N and O atoms with carbon nanotubes," *Chemical Physics Letters*, 374, 2003, pp. 501-505.

Chongwu Zhou et al., "Modulated Chemical Doping of Individual Carbon Nanotubes," *Science*, vol. 290, Nov. 24, 2000, pp. 1552-1555.

J.P. Novak et al., "Nerve Agent Detection Using Networks of Single-Walled Carbon Nanotubes," *Applied Physics Letters*, vol. 83, No. 19, Nov. 10, 2003, pp. 4026-4028.

Chongwu Zhou et al., "Modulated Chemical Doping of Individual Carbon Nanotubes," *Science*, vol. 290, Nov. 24, 2000, pp. 1552-1555.

S. Chopra et al., "Carbon-nanotube-based resonant-circuit sensor for ammonia," *Applied Physics Letters*, vol. 80, No. 24, Jun. 17, 2002, pp. 4632-4634.

Jing Kong et al., "Chemical profiling of single nanotubes: Intramolecular p-n-p junctions and on-tube single-electron transistors," *Applied Physics Letters*, vol. 80, No. 1, Jan. 17, 2002, pp. 73-75.

Phillip G. Collins et al., "Extreme Oxygen Sensitivity of Electronic Properties of Carbon Nanotubes," *Science*, vol. 287, Mar. 10, 2000, pp. 1801-1804.

* cited by examiner

OXYGEN-CHEMICAL AGENT SENSOR

CROSS-REFERENCE TO RELATED APPLICATIONS

The present invention claims priority under 35 U.S.C. §119 (e) to U.S. Provisional Patent Application Ser. No. 60/589,408 filed Jul. 20, 2004.

TECHNICAL FIELD

The present invention relates in general to gas sensors, and in particular to oxygen and chemical agent gas sensors using carbon nanotube cathodes.

BACKGROUND INFORMATION

Most of the present-day gas sensors based on carbon nanotubes are conductometric, that is, a response of the sensor based on the resistance change due to contact with the gas. That change is usually due to a doping process.

The electrochemical sensors which are popular fail in sensing oxygen in aircraft engines, due to the lack of accuracy and contaminants from interfering fuel vapors. The "wet" electrochemical sensor has inherent disadvantages of leakage and the "dry" electrochemical sensors with solid electrolytes (e.g., cationic and anionic membranes, xerogels) have lesser sensitivity and are influenced by humidity and temperature. There is a need for an inexpensive sensor that can operate in high temperature, pressure conditions, that can be inert towards fuel gas vapors and they can have increased accuracy towards the detection of oxygen in fuel tanks.

As a result of the foregoing, there is a need in the art for a sensor to monitor oxygen content. The sensor should be unaffected should it come in contact with either fuel vapors or the fuel itself. The explosive limit of oxygen such as in aircraft fuel tanks is between 9-12%, however an efficient sensor should be able to detect <9% and >12% of oxygen in the aircraft fuel tanks. The sensor should have low maintenance, high reliability, low cost and reasonable recovery times. The normal electrochemical sensors attractive for the detection of various gases are not suitable for this application, due to the possible contamination of the electrolyte with the fuel vapors.

Other needs for related gas sensors occur in automotive and commercial combustion control systems, where the amounts of residual oxygen in the effluent gasses must be measured. In other applications, there is a need to detect chemical warfare (nerve) agents to counter terrorism. The chemical warfare agents are mostly nucleophiles (electron donors) and need to be detected in ppb (parts per billion) concentrations. The accurate detection of these chemical species is essential for the safety of human life in protecting the general public from possible terrorist attacks using chemical warfare agents.

Present-day conductometric sensors cannot distinguish between different electron donating or electron accepting species. This leads to cross-sensitivity or interference between the different gaseous species. In view of theses findings, there is a need in the art for a highly selective sensor for the detection of electrophile (e.g., oxygen and other electron acceptors) and nucleophile (e.g., chemical warfare agents and other electron donors) gases. Furthermore, a sensor using a diode characteristic as the electronic detection mechanism, instead of the standard conductometric mechanism, could provide higher sensitivity and lower detection limits.

SUMMARY OF THE INVENTION

The present invention addresses the foregoing need by providing a novel method and a new device for sensing electron-accepting gases such as oxygen and certain electron-donating nerve agents (e.g., DMMP and sarin). The sensor can detect trace amounts of the gasses, down to parts-per-billion. Example applications for the sensor include use as a combustion controller, such as for an automobile, or as a detector of potentially explosive ratios of oxygen and fuel in a fuel tank, such as an aircraft fuel tank.

The sensing mechanism of the present invention uses carbon nanotubes, which exhibit a resistance change in the presence of electron-acceptor gasses. In such a mode, the entire semiconducting nanotube is exposed to the gas, which effectively dopes it to become a p-type material, changing its conduction (resistance) behavior. The present invention greatly enhances this resistive effect by creating a P—N diode junction. This gives far greater sensitivity, and also provides a means to distinguish between the gas type being sensed.

When applied as a fuel tank sensor, the following advantages apply. The aviation fuel vapor consists of numerous hydrocarbon components, comprising paraffins, plefins, naphthenes, aromatics, together with sulphur and nitrogen compounds. (*Aviation Fuels Technical Review Appendix B: About Hydrocarbons*, FTR-3, Chevron Products Corp., 2000). The nanotube-based sensing mechanism is unaffected by aviation fuel gas vapors, since the conversion of the neutral to p-type behavior arises only due to the high electrophilic nature of oxygen. The detection mechanism based on diode characteristics, such as the diode knee, offers a certain selectivity to oxygen in that the knee voltage will be dependent upon the adsorbing species. This provides selectivity not available with the chemo-resistor based sensors.

The same device can sense electron-donating gas species, including nerve agents. Some detectable electron donating nerve agents include, but are not limited to, sarin, tabun, DMMP (dimethyl methane phosphonate), a simulant for sarin, chlorine, hydrogen cyanide, and soman. By measuring the characteristic diode I—V curve (or the disappearance of it), the specific gases can be identified.

The descriptions in this document discuss sensing of an electron-accepting gas, such as oxygen. However, an alternative configuration is possible in which P or N dopings are reversed. With a suitable oxygen-blocking membrane, the sensor of this invention could detect electron-donating gasses, such as sarin, DMMP, or other nerve agents. As such, the foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, the advantages thereof, reference is now made to the following descriptions taken in conjunction with the accompanying drawings, in which.

DETAILED DESCRIPTION

In the following description, numerous specific details are set forth such as specific substrate materials to provide a thorough understanding of the present invention. However, it will be obvious to those skilled in the art that the present invention may be practiced without such specific details. In other instances, well known circuits have been shown in block diagram form in order not to obscure the present invention in unnecessary detail. For the most part, details concerning timing considerations and the like have been omitted inasmuch as such details are not necessary to obtain a complete understanding of the present invention and are within the skills of persons of ordinary skill in the relevant art.

Refer now to the drawings wherein depicted elements are not necessarily shown to scale and wherein like or similar elements are designated by the same reference numeral through the several views.

Carbon nanotubes (CNTs) are extremely oxygen sensitive, and that oxygen adsorbed on single-walled semiconducting nanotubes (SWNTs) changes the doping levels of the nanotubes. Further, this doping is effectively a p-type doping, and changes the resistance of the nanotubes. The present invention creates a P—N junction within the nanotube, but causes that junction to appear only in the presence of oxygen. By creating a temporary diode on the SWNT, rather than a simple resistance change by the presence of oxygen, the sensor is made more sensitive and flexible. In a SWNT without the diode formed on it, the resistance (approximately 9000 ohms/ micron, when fully saturated in oxygen) changes a small but measurable amount when oxygen is present. When the diode of the present invention is used, the change is drastic, with heavy hole (p-type) conduction rather than the small change in electron (n-type) conduction In the following description, any reference to 'oxygen' may be substituted with any electron-accepting gas. Oxygen is used for the sake of simplicity. The invention is equally applicable to electron donor gasses by swapping the diode P—N configuration.

Previous efforts on the development of oxygen sensors were based on potentiometric sensing mechanism involving polymers. (*Reliable, maintenance-free oxygen sensor for aircraft using an oxygen-sensitive coating on potentiometric electrodes*, De Castro, E. S.; Meyerhoff, M. E. Aquanautics Corp., Alameda, Calif., USA. Avail. NTIS. Report (1990), (USAFSAM-TP-89-20; Order No. AD-A222696), 28 pp. From: Gov. Rep. Announce. Index (U.S.) 1990, 90(20), Abstr. No. 050,711). They are not readily compatible to hostile fuel tank environments. In the prior art, a RF modulation spectroscopy of a near-IR tunable laser diode source with temperature and pressure compensation was also developed to measure oxygen contents in aircraft. (Cooper et al., U.S. Pat. No. 5,572,031). However this technique involved the calibration with a reference cell and relied on expensive equipment.

In one application, a method and device of the present invention are useful both where there is a need to detect whether oxygen concentration is within a specific range, and where the actual percentage of oxygen needs to be determined with accuracy. In one instance, while the oxygen-fuel ratio at the inlet to an automotive fuel system is relatively easy to estimate on the basis of air and fuel volumes, the ratio of oxygen in the exhaust cannot be so accurately deduced. The oxygen content must be measured for accurate determination. Measuring the oxygen levels in the exhaust, with a device as in one embodiment of the present invention, permits the combustion efficiency to be monitored, which in turn allows real-time control of the air-fuel ratios as needed for optimal compensation. In another example, application of the present invention, when the fuel level in aircraft tanks is in the range of 9-12% by volume, there is a potentially explosive mixture present. Military aircraft use a nitrogen-gas purge to eliminate oxygen in the tank. With an instrument based on the present invention monitoring the oxygen concentration levels, the purge can be automatically triggered, thereby preventing the oxygen level from reaching dangerous levels. The present invention is compatible with the fuel vapors and with the extreme pressure and temperature conditions in aircraft fuel tanks.

The present invention relates to a 2-wire sensor device whose associated electronics are also very simple. The invention uses modified carbon nanotubes as the sensing material. The carbon nanotubes have high specificity towards the adsorption of oxygen and are excellent sensing materials due to their high specific surface area and extraordinary electronic properties. The underlying features of the present invention also enable sensitivity to any electron-donating species, such as other gasses that may include nerve agents and the like. The current vs. voltage characteristic of the resultant diode can be measured to determine which type of gas is present, whereby the 'knee' in this curve is the indicative electrical feature. The resulting diode-style sensor can be made selective to other gasses besides oxygen by the inclusion of a cover membrane that can selectively distinguish between various electron-accepting species.

A simple electronic two-terminal sensing system for oxygen is made possible by properly treating semiconducting CNTs. One sensing mechanism based on a single nanotube is disclosed, but the approach can be extended to multiple arrays of nanotubes. The electronics simply measure the conduction of CNTs (change in carrier concentrations), distinguishing between a weak resistive conduction (no oxygen) and a diode-like forward conduction (in oxygen). The circuitry for sampling I—V characteristics, whereby a positive and negative bias is applied, and the resulting current flow is measured, with calculation and storage of critical parameters such as knee voltage, is well known in the art. Operation over a broad temperature range is possible, and no liquid environment is necessary, as when using conventional potentiometric techniques.

The device related to the present invention consists of CNT(s) bridging two gold electrodes on an inert surface.

Figure 1:
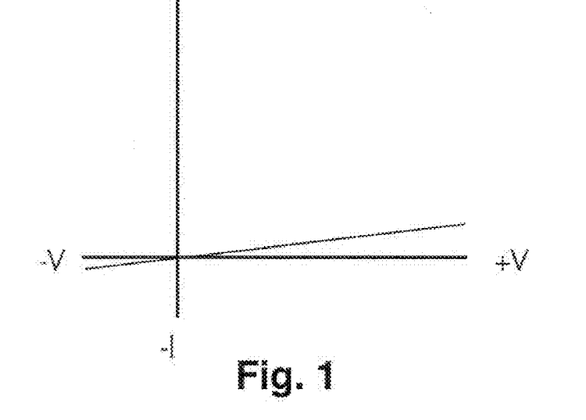
FIG. 1 illustrates an I—V curve for an I—N doped CNT sample of an embodiment of the present invention.
Figure 2:
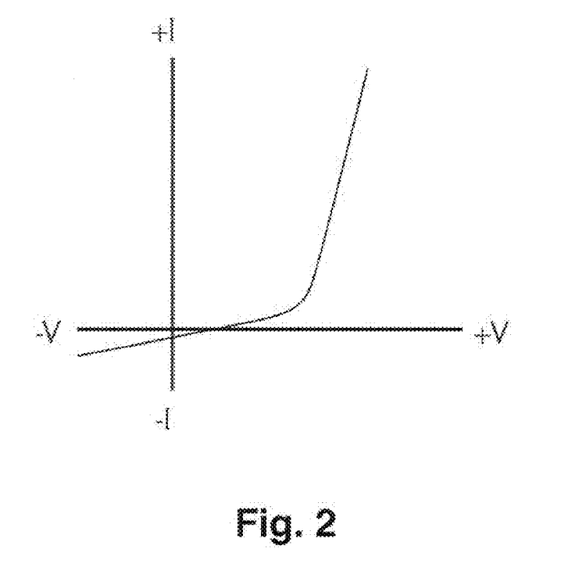
FIG. 2 illustrates an I—V curve for a P—N doped (oxygen-exposed) CNT sample of an embodiment of the present invention.

Oxygen is chemically active and adsorbs onto the CNT surface, effectively doping the CNT to become a p-type material by creating semiconductor holes. Without oxygen bound to the CNT, the CNT is effectively an undoped intrinsic (i-type) material. We propose to dope half the CNT with potassium, to make that half of the nanotube n-type, adding mobile electrons to the material. Doping would be heavy enough to fill the majority of the binding sites on the n-type half of the CNT. This process creates a CNT that has an I—N junction, a highly resistive path with low conductivity. In the presence of oxygen, oxygen selectively binds to the i-type half to form a P—N junction, which results in a diode. FIG. 1 shows the current vs. voltage (I—V) curve for a CNT with an I—N junction, which has not been exposed to oxygen. Note that the current rises very slowly as voltage is increased in the positive direction, without exposure to oxygen. FIG. 2 shows the current vs. voltage (I—V) curve for a CNT with an P—N junction which was created as a result of exposure to oxygen. Note that the current rises sharply as a positive bias voltage is applied. The inflection point where the conductivity behavior changes to a conductor with low resistivity is the 'knee' of the I—V curve and can be a characteristic of the p-type dopant. This type of device is very selective to oxygen.

Figure 9A:
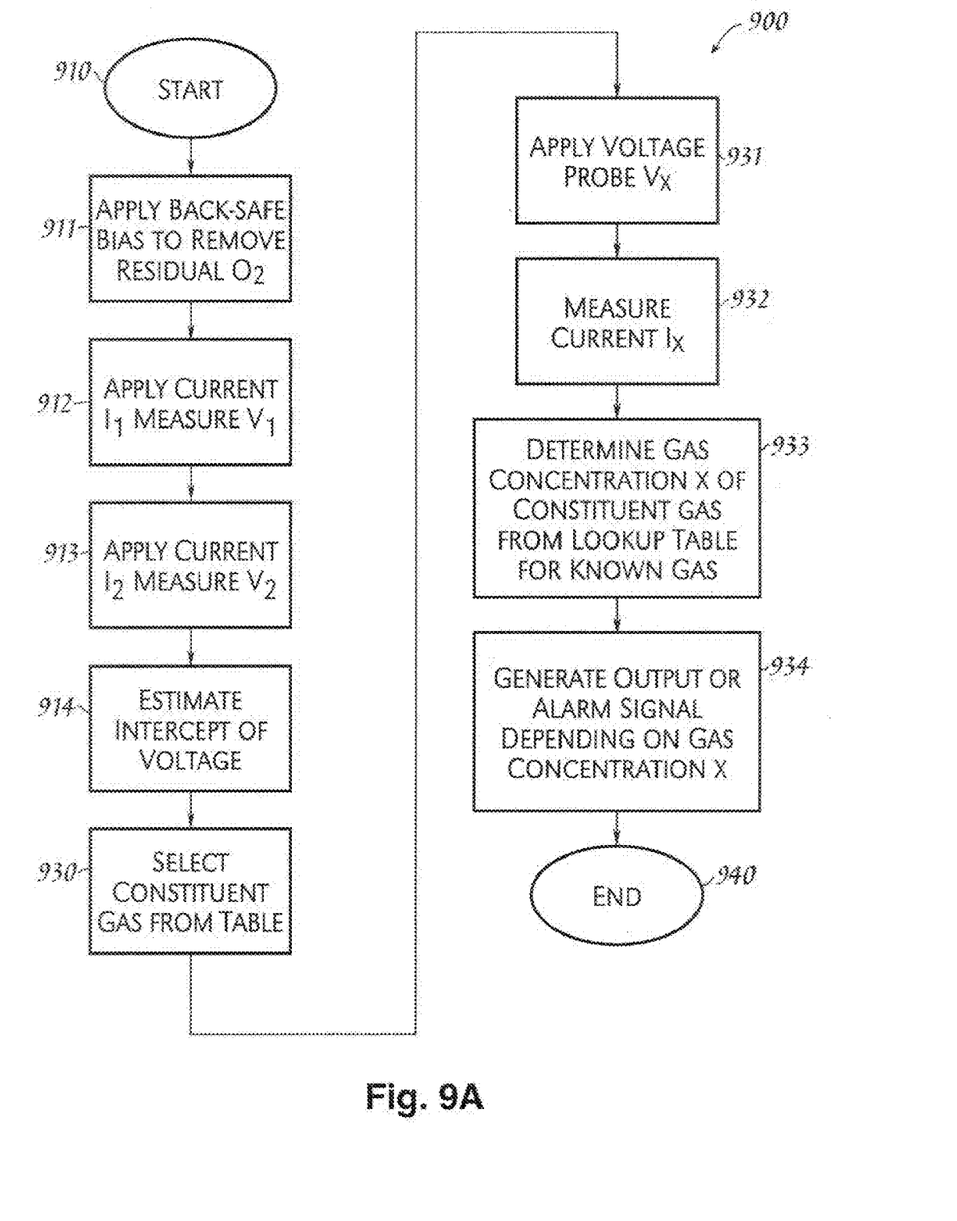
FIG. 9A illustrates an algorithmic flow of operations in the signal processing circuitry in an embodiment of the present invention.
Figure 10:
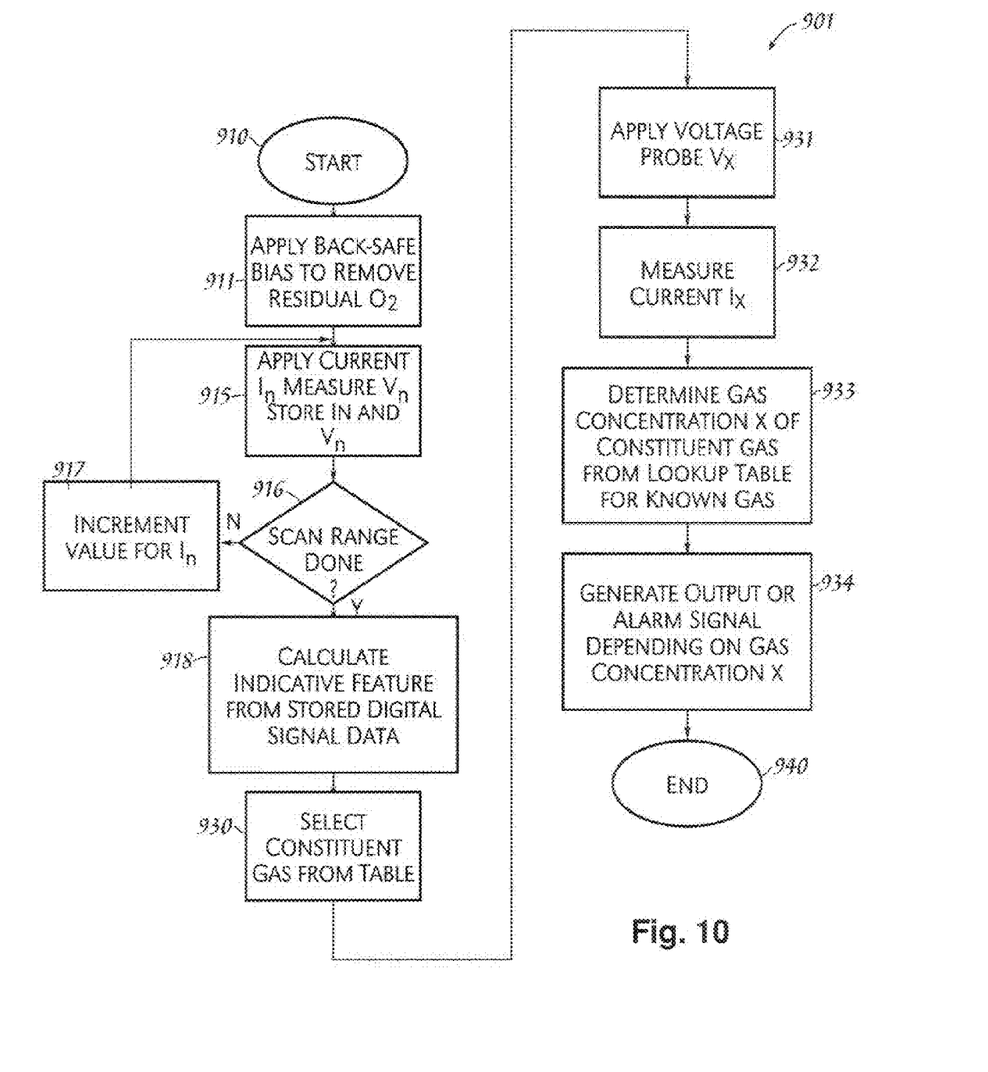
FIG. 10 illustrates an algorithmic flow of operations in the signal processing circuitry in an embodiment of the present invention.

The difference between the curves illustrated in FIG. 1 and FIG. 2 can be readily detected by very simple circuits. Demonstrative examples of algorithms 900, 901 for detecting gas concentration based on I—V curves are illustrated in FIG. 9A and FIG. 10. The present invention provides a significant improvement over conductometric methods by using the diode configuration in logarithmic mode, thereby enabling parts per billion detection. Factors which require compensation of the sensing mechanism for a given dopant (i.e., gas to be detected) include a characterization (i.e., calibration) of the I—V curve and modification of the doping to permit measurement at the required concentration. In one example, the doping is selected to provide an optimal detection signal for the concentration range of 9-12% oxygen gas.

Figure 9B:
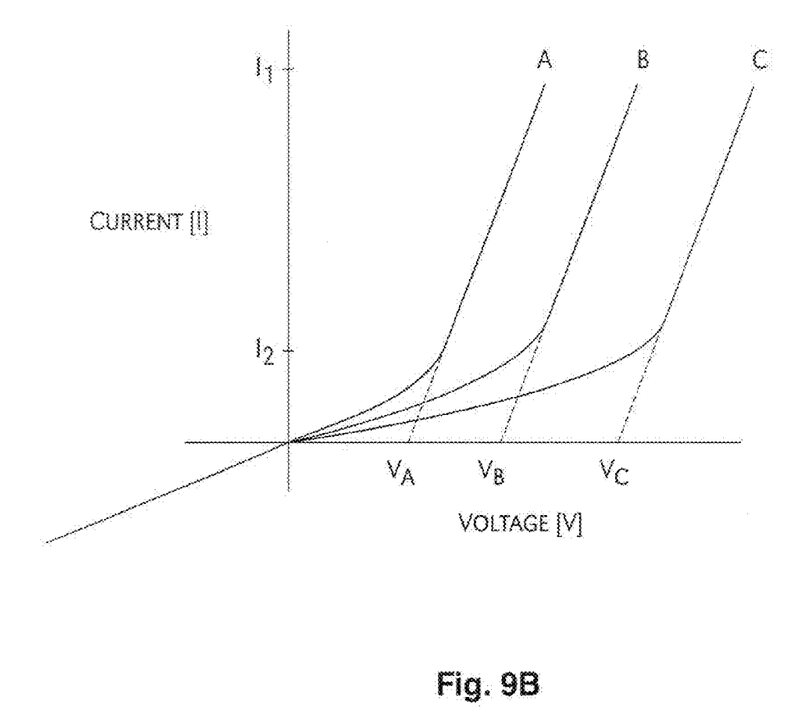
FIG. 9B illustrates I—V curves and their voltage intercepts for different gasses in an embodiment of the present invention.

The absolute position of the 'knee' voltage of the diode curve, the approximate point on the voltage axis at which the curve flexes upwards, can also give confirmation that the doping gas is indeed oxygen (or any other calibrated gas). By equipping the sensing mechanism with characteristic data for one or several doping gases, selectivity of the sensor can be determined. As shown in FIG. 9A and FIG. 10, by implementing the appropriate circuitry, the sensing mechanism 900, 901 can be flexibly determined using the appropriate steps to acquire and interpret the signal data 912-918, and generate a desired response, such as a detection alarm signal 934. An example of the algorithmic flow of signal processing circuitry 900 in one embodiment of the present invention is illustrated in FIG. 9A. In FIG. 9A, an algorithm 900 is implemented comprising measuring two points 912, 913 along the I—V curve to determine the slope line, then extrapolating the slope line linearly to determine the voltage intercept 914. Then, the gas corresponding to the computed voltage intercept, which is a characteristic value for that gas, is selected 930 from a table. In this manner, the sensor can be made selective to a specific gas species. In FIG. 9B, this method is shown graphically for examples of gasses A, B, and C, which cause distinct 'knee' voltage changes in the I—V characteristic of the diode curves to be exhibited by the resulting diode structure when they are present as dopants in a semiconducting SWNT. After the gas has been identified in step 930, the normal operation of the sensing mechanism proceeds by applying a probe voltage 931 and measuring the resultant current 932, from which the concentration of the gas can be determined 933. Depending on the detected concentration of the gas, an output signal or alarm can be generated 934 by the device.

FIG. 10 illustrates an algorithm 901 in another example of the present invention comprising the registration 915 of the entire I—V curve across a given range 916, 917. From the stored digital data of the I—V signal, as shown in FIG. 10, an indicative feature can be calculated 918 to determine selectivity for a specific gas 930. The indicative feature can be determined from calculations 918 that comprise linear interpolation of a segment of the I—V curve, non-linear methods, or other signal processing steps. In one example of a calculation 918 of such an indicative feature, the $1^{st}$ and $2^{nd}$ derivatives of the I—V curve are calculated and further used to determine the exact position of the diode 'knee'. Other features of the diode curve, either theoretical or empirically determined, can be used as indicative features for such calculations 918 from previously registered I—V signal data. The remaining steps of the algorithm 901 are similar to a previous example 900. Embodiments of the present invention can rely on algorithms which are implemented in circuitry or circuitry that is responsive to software.

The selectivity of the sensing mechanism to a specific chemical species can be further enhanced by use of a filter coating of chemoselective polymer films, which can be tailored to distinguish between electron donating or electron accepting species. In one example, a filter coating is used to select sensitivity of the sensing mechanism among different electron accepting species. In one case, a fluoroalcohol substituted polycarbosilane, which are hydrogen bond acidic materials with exceptional thermal and chemical stability, comprises the filter coating.

The prior art provides important knowledge about the interaction of oxygen molecules with carbon nanotubes. Transport measurements and scanning tunneling spectroscopy confirmed that the electrical resistance, thermoelectric power, and local density of states of carbon nanotubes can be influenced by the exposure to oxygen. (Collins et al., Science, 287(5459), 1801-1804, 2000). The oxygen molecules were also found to adsorb physically onto the defect-free semiconducting single walled nanotubes and increase their conductance. The chemisorption of oxygen onto defect-free nanotubes has a relatively smaller change in the conductance. (Grujicic et al., Surface Science, 211(1-4), 166-183, 2003). The oxygen—single walled nanotube interaction arises from van der Waals forces as suggested by the molecular mechanics calculations. (Ulbricht et al., Surface Science, 532-535 852-856, 2003). The adsorption of oxygen onto the single walled carbon nanotubes (SWNTs) is shown to affect their transport properties with the interaction depending on spin configuration that in turn specifies the path of oxygen adsorption. Indeed, the same adsorption mechanism will also work with any electron-donating gas species, permitting use as a sensor for chemical nerve agents since the electron donors cause a change in conduction in the SWNTs. The adsorption geometry is found to depend sensitively on the curvature of the nanotubes. (Froudakis et al., Physical Review B: Condensed Matter and Materials Physics 68(11), 115435/1-115435/5, 2003). In the case of a single oxygen atom, the most stable adsorption site is one in which the O atom sits on a C—C bridge, breaking the underlying C—C bond. (Collins et al.) These properties of oxygen adsorption onto single walled carbon nanotubes to create an oxygen sensing mechanism for use in aircraft fuel tanks and other applications is the basis of the present invention.

The principle sensing mechanism involves the semiconducting behavior of doped CNTs. The single walled carbon nanotubes (SWNTs) can be doped selectively to obtain P—N (or N—P) junctions across the length of the nanotubes. (Zhou et al., Science 290, 1552, 2000). The p-type conductivity of a semiconducting nanotube arises due to the adsorption of molecular oxygen from the ambient atmosphere. (Kong et al., Applied Physics letters, 80, 73, 2002). One option for degassing the SWNTs is by heating under high vacuum to remove the adsorbed gases on the nanotubes. The degassing of the nanotubes can be carried out by heating the nanotubes up to 110-150° C. under high vacuum for several hours. (Collins et al.). While the removal of adsorbed oxygen may not be complete by this process, the step prepares the tubes for the predominating n-doping to follow. In one example, the subsequent n-doping forms an n-type semiconductor over residual p-type oxygent dopant.

The degassed nanotubes will remain intrinsic (i.e., undoped) and these nanotubes can be selectively doped over one half of their length by an organic or alkaline dopant using a suitable mask on the other half. (Grujicic et al.). In one example, a potassium dopant was used with a PMMA mask covering half of the CNT. The doping converts one half of the nanotube n-type leaving the other half intrinsic. The I—V curve for this kind of response would be linear, resembling a resistor. In the presence of oxygen (or other electrophilic species), the intrinsic part of the nanotube becomes p-type due to the adsorption of the oxygen atoms (electrophile) onto the nanotubes. The n-type half of the nanotube remains unaffected due to the presence of oxygen. The nanotube, then effectively becomes a P—N junction diode, with the I—V response of the nanotube showing a typical diode characteristic. The transition in the conductivity characteristic of the semiconducting nanotube from I—N to P—N is as illustrated in FIG. 1 and FIG. 2 respectively.

Figure 3:
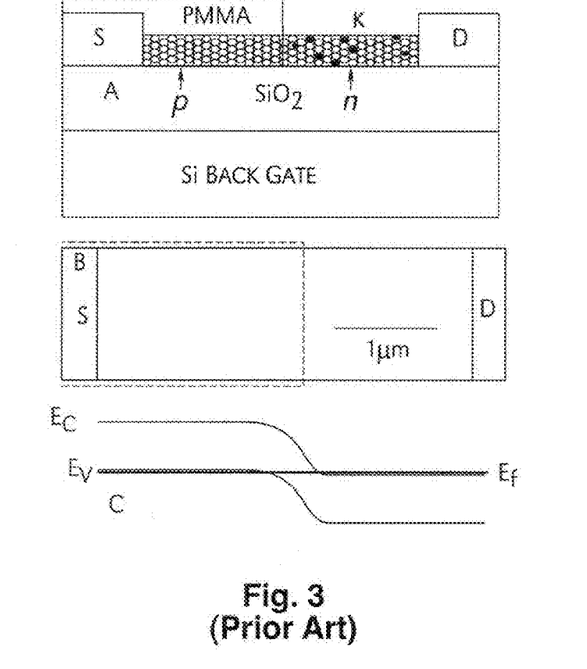
FIG. 3 illustrates a prior art example of modulated doping in SWNTs.

A prior art example of modulated chemical doping of SWNTs is shown in FIG. 3. (Zhou et al.). The present invention represents a fundamentally different approach from that illustrated in FIG. 3 by starting with the degassed tubes, which are i-type, and doping one half of the tube to n-type. The sensing mechanism is created via the remaining undoped half of the nanotube. The present invention involves various steps for forming the required I—N and P—N junctions. For the following examples and enclosed figures, a single SWNT is shown for clarity. Essentially similar results are obtained with CNT 'felt' mats, in other examples of the present invention. The SWNTs may be either semiconducting or metallic, depending upon the method of growing them. For this process, we shall use commercially available SWNTs that have been significantly purified to reduce the metallic-SWNT content. Concentrations approaching 80% semiconducting SWNTs are available, with the remaining metallic tubes removed as discussed below. Either aligned SWNTs or thick mats of random (non-aligned) SWNTs may be used for the sensor. Only SWNTs that bridge the two contacts are active nanotube elements. For example, for 10 µm nanotubes, a 5 µm gap between electrodes may be optimal. The electrode spacing should be proportional to the length of the nanotubes.

Figure 4:
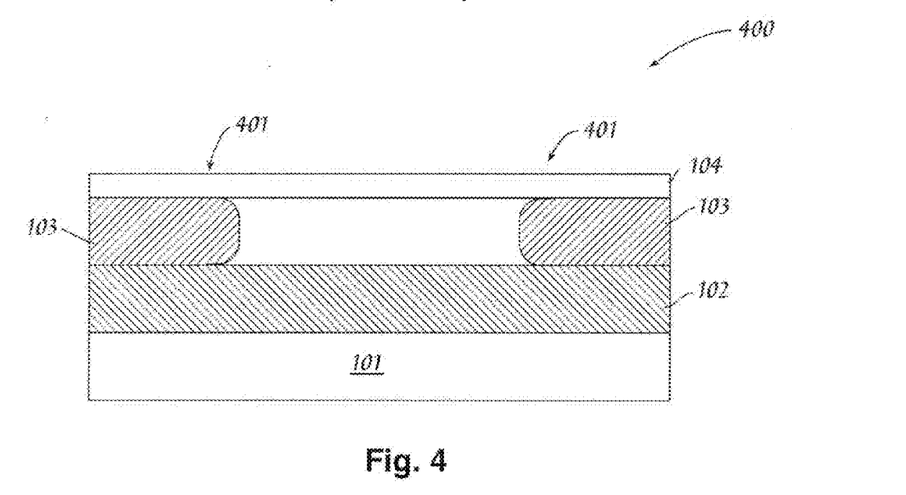
FIG. 4 illustrates an implicitly p-doped CNT structure in an embodiment of the present invention.

In FIG. 4, the SWNT(s) 104 are attached between gold contact pads 103 on a $SiO_2$ substrate layer 102. The figures are all shown an additional silicon substrate 101 (that acts as a gate) below the $SiO_2$ layer 102. The gate is not mandatory, but may be used for both establishing the DC parameters of the sensor and for back-bias removal of adsorbed gasses. The nanotubes are assumed to be formed in an oxygen atmosphere, or to have been exposed to oxygen, which is the normal condition for SWNTs. The implied doping 400 for the oxygen-adsorbed nanotube is therefore p-type 401, as indicated.

Figure 5:
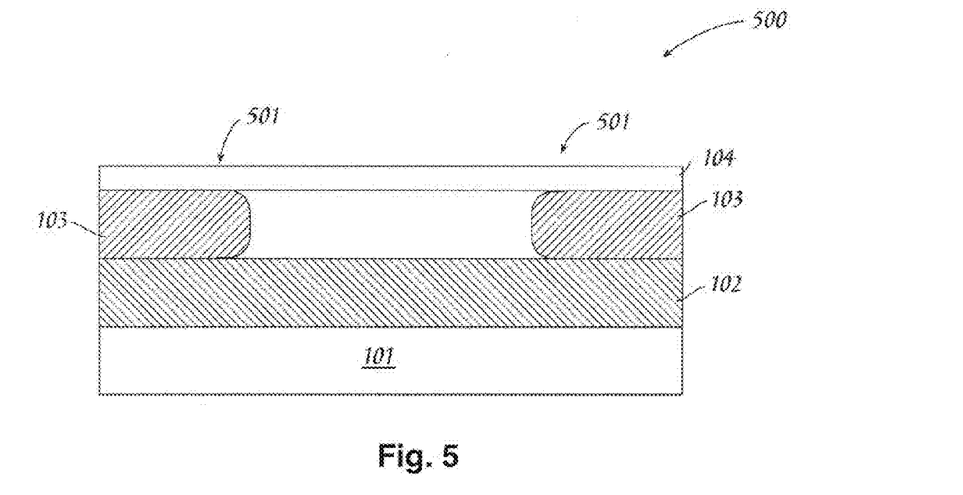
FIG. 5 illustrates a degassed CNT structure in an intrinsic state in an embodiment of the present invention.

The next step 500, as illustrated in FIG. 5, is to remove the oxygen from the SWNTs 104, causing them to revert to their un-doped state, noted as intrinsic or i-doped state 501. This is done by degassing them at an elevated temperature and high vacuum, resulting in the conditions shown FIG. 5. A majority of adsorbed oxygen is thereby released. Another method of removal is the use of a backgate 101 with application of a high bias on a backside electrode. (Novak et. al., Appl. Phys. Ltrs, 83, 4026, 2003). After the step illustrated in FIG. 5, predominately resistive i-type SWNTs are present, and a small percentage of them are also metallic. The prior art consistently discloses the resistance of p-type SWNTs to be on the order of 9 kOhms per micron, which is fairly high. The resistance of remaining metallic tubes would be much lower. It is well known in the art that residual metallic nanotubes may be removed by passing small AC current through the contacts 911, with an amplitude just high enough to 'pop' the metallic SWNTs, removing them from the device. The higher resistance of the p- and i-type nanotubes limits the current to non-destructive levels for the remaining CNTs.

Figure 6:
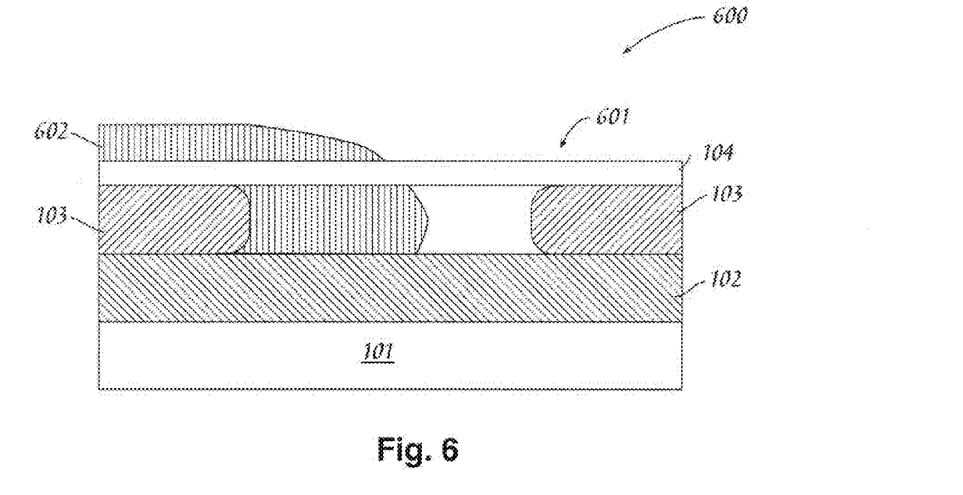
FIG. 6 illustrates PMMA masking during potassium doping of a CNT structure in an embodiment of the present invention.
Figure 7:
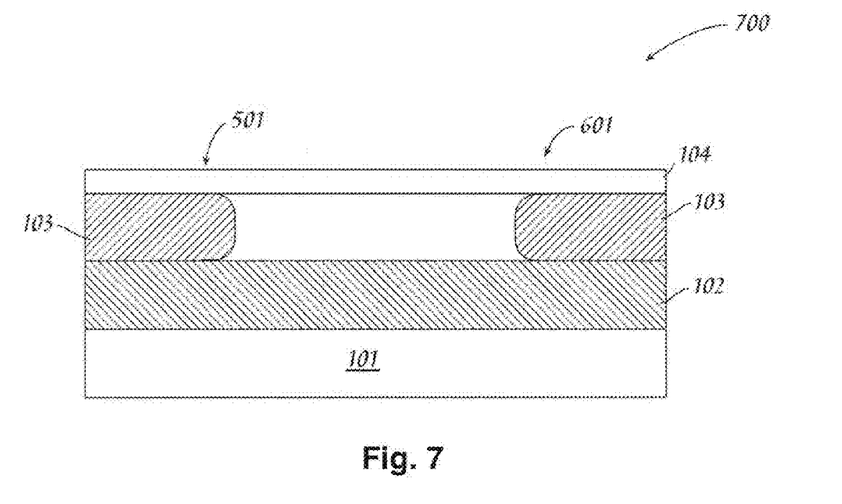
FIG. 7 illustrates mask-stripped I—N doped CNT structure in an embodiment of the present invention.

In the next step 600, as illustrated in FIG. 6, half of the nanotube (or nanotube felt) is then coated in PMMA photoresist 602, while the other portion of the nanotube(s) are then doped with potassium 601 or other electron donors to make it into n-type material. The PMMA overcoat 602 is then stripped 700 as shown in FIG. 7 to reveal SWNTs 104 that have an I—N boundary/junction. On one side the CNT is n-doped 601, in one case with potassium, while on the other side the CNT is the undoped i-type 501. At this stage, the nanotubes behave as weak resistors, exhibiting an essentially linear I—V curve corresponding to FIG. 1. Stripping 700 is rapid but is done in an oxygen-free environment, to minimize re-doping 401 by oxygen. Complete re-doping occurs in about 10-20 minutes in an oxygen rich environment, such as air. (Collins et al.)

Figure 8:
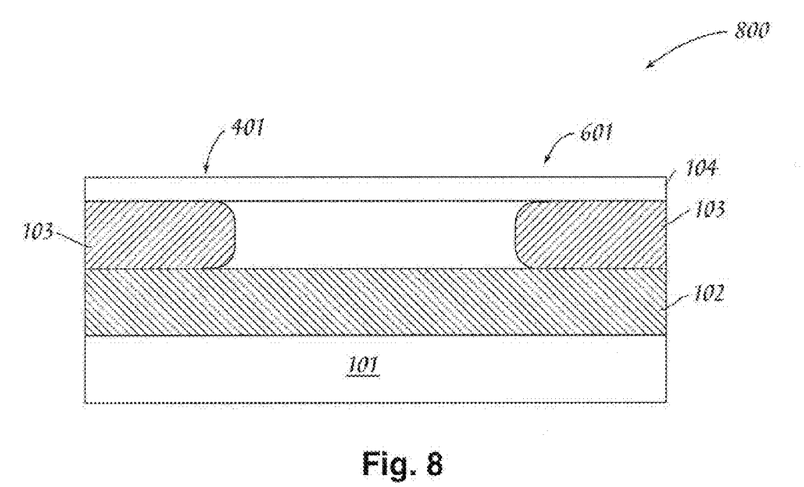
FIG. 8 illustrates a P—N junction formed upon oxygen exposure of a CNT structure in an embodiment of the present invention.

When the I—N junctioned SWNT is exposed to oxygen 800, as shown in FIG. 8, the i-type 501 material turns to p-type material 401, in proportion to the amount of oxygen present. That is, it turns from a resistive device to a diode device, such that its characteristic conductance curve changes from the one in FIG. 1 to that shown in FIG. 2. This change forms the basis of the sensing mechanism that the attached circuitry is easily able to detect. The external electronics detect the characteristic of the I—V curve, and in one example, yield a current signal proportional to the oxygen-derived p-doping. In another example, a felt-like mat of SWNTs are used instead of a single nanotube, and the I—V characteristic may vary. It is possible that if oxygen adsorption is not completely removed prior to the n-doping as shown in FIG. 6, the diode junction doping profile will be sufficiently altered so as to reduce the ultimate sensitivity of the sensor. In one embodiment of practicing the present invention, a back-gate biasing step, or thermal means, are used to ensure adequate removal of oxygen prior to n-doping. In another instance, prior to use of the sensor in a presumed oxygen-free environment, such as an aircraft fuel tank, the back-gate bias is reapplied to remove any adsorbed oxygen.

In other semiconducting configurations of the nanotube sensing mechanism, selectivity for nucleophilic electron donor gasses, such as some nerve agents, is created by replacing the n-type dopings illustrated in FIGS. 6, 7, and 8 with p-type dopings. An additional step to create an electron donor sensor may include applying an oxygen blocking membrane after PMMA is stripped over the remaining undoped portion of the SWNTs, thereby preventing p-doping by oxygen.

Although the present invention and its advantages have been described in detail, it should be understood that various changes, substitutions and alterations can be made herein without departing from the spirit and scope of the invention as defined by the appended claims.

What is claimed is:

1. A gas sensing device for selectively detecting electrophilic species comprising:
    an insulating substrate;
    two conducting electrode pads deposited on said substrate, separated by a gap greater than about 10 nm; and
    semiconducting carbon nanotube material deposited on said two electrode pads forming a conduction path, wherein about one half of said carbon nanotube material is in an undoped, instrinsic i-type electronic state and the remaining portion of said nanotube material is doped with a nucleophilic species to form an n-type semiconductor, such that an I—N junction is formed, wherein a P—N junction diode is formed in the presence of said electrophilic species; and
    circuitry connected to said electrode pads for measuring the conductivity characteristics of the diode structure, wherein the circuitry is configured to detect the presence of said electrophilic species by detecting the presence of a knee in a current-voltage curve for the semiconducting carbon nanotube material.

2. The device of claim 1, wherein the carbon nanotube material comprises single-walled carbon nanotubes.

3. The device of claim 1, further comprising:
    a backgate electrode layer connected to the diode structure for applying a DC bias to the diode structure.

4. The device of claim 1, further comprising:
    a filter coating of chemoselective film applied on the i-type portion of the carbon nanotube material.

5. The device of claim 1, wherein the electrophilic species comprises oxygen gas, chemical warfare agents, or other electron acceptor gasses.

6. The device of claim 1, further comprising:
    circuitry for detecting individual electrophilic species by registering and analyzing said conductivity characteristics of said individual electrophilic species; and
    circuitry for providing an output signal upon said detecting of said individual electrophilic species.

7. A gas sensing device for selectively detecting nucleophilic species comprising:
    an insulating substrate;
    two conducting electrode pads deposited on said substrate, separated by a gap greater than about 10 nm; and
    semiconducting carbon nanotube material deposited on said two electrode pads forming a conduction path, wherein about one half of said carbon nanotube material is in an undoped, instrinsic i-type electronic state and the remaining portion of said nanotube material is doped with an electrophilic species to form a p-type semiconductor, such that an I—P junction is formed, wherein an N—P junction diode is formed in the presence of said nucleophilic species; and
    circuitry connected to said electrode pads for measuring the conductivity characteristics of the diode structure, wherein the circuitry is configured to detect the presence of said nucleophilic species by detecting the presence of a knee in a current-voltage curve for the semiconducting carbon nanotube material.

8. The device of claim 7, wherein the carbon nanotube material comprises single-walled carbon nanotubes.

9. The device of claim 7, further comprising:
    a backgate electrode layer connected to the diode structure for applying a DC bias to the diode structure.

10. The device of claim 7, further comprising:
    a filter coating of chemoselective film applied on the i-type portion of the carbon nanotube material.

11. The device of claim 7, wherein the nucleophilic species comprises sarin, tabun, DMMP, soman, other chemical warfare agents or other electron donating gasses.

12. The device of claim 7, further comprising:
    circuitry for detecting individual nucleophilic species by registering and analyzing said conductivity characteristics of said individual nucleophilic species; and
    circuitry for providing an output signal upon said detecting of said individual nucleophilic species.

13. The device of claim 1, wherein the circuitry is configured to identify the electrophilic gas by determining a voltage intercepted by a slope line of a portion of the current-voltage curve that is beyond the knee and correlating the electrophilic gas to an electrophilic gas having a calibrated voltage intercept that corresponds to the voltage intercept determined.

14. The device of claim 7, wherein the circuitry is configured to identify the nucleophilic gas by determining a voltage intercepted by a slope line of a portion of the current-voltage curve that is beyond the knee and correlating the nucleophilic gas to a nucleophilic gas having a calibrated voltage intercept that corresponds to the voltage intercept determined.

15. The device of claim 1, wherein the circuitry is configured to measure the concentration of the electrophilic gas in parts per billion after the electrophilic gas has been identified as a calibrated electrophilic gas by applying a probe voltage and measuring a resulting current and determining the concentration of the electrophilic gas from a lookup table for the calibrated electrophilic gas using the applied voltage and the measured current.

16. The device of claim 7, wherein the circuitry is configured to measure the concentration of the nucleophilic gas in parts per billion after the nucleophilic gas has been identified as a calibrated nucleophilic gas by applying a probe voltage and measuring a resulting current and determining the concentration of the nucleophilic gas from a lookup table for the calibrated nucleophilic gas using the applied voltage and the measured current.

* * * * *